US007241577B2

(12) United States Patent
Seifer et al.

(10) Patent No.: US 7,241,577 B2
(45) Date of Patent: Jul. 10, 2007

(54) MULLERIAN INHIBITING SUBSTANCE LEVELS AND OVARIAN RESPONSE

(75) Inventors: David B. Seifer, Holmdel, NJ (US); David T. MacLaughlin, Saugus, MA (US)

(73) Assignees: University of Medicine and Dentistry of New Jersey, New Brunswick, NJ (US); The General Hospital Corporation, Boston, MA (US)

( * ) Notice: Subject to any disclaimer, the term of this patent is extended or adjusted under 35 U.S.C. 154(b) by 112 days.

(21) Appl. No.: 10/225,503

(22) Filed: Aug. 20, 2002

(65) Prior Publication Data

US 2003/0124620 A1 Jul. 3, 2003

Related U.S. Application Data

(60) Provisional application No. 60/313,545, filed on Aug. 20, 2001.

(51) Int. Cl.
*G01N 33/53* (2006.01)
*C07K 14/00* (2006.01)

(52) U.S. Cl. ..................... 435/7.1; 435/7.21; 435/7.92; 436/501; 530/397; 530/399

(58) Field of Classification Search ................ 435/7.1, 435/7.21, 7.92; 436/501; 530/397, 399
See application file for complete search history.

(56) References Cited

U.S. PATENT DOCUMENTS

| 4,792,601 A | 12/1988 | Donahoe et al. |
| 5,310,880 A | 5/1994 | Donahoe et al. |
| 5,547,854 A | 8/1996 | Donahoe et al. |

OTHER PUBLICATIONS

Fallat et al. Fertility and Sterility, vol. 67, No. 5, May 1997, pp. 962-965.*
Khamsi et al. Endocrine, Aug/ 1998, vol. 9, No. 1, pp. 15-25.*
Donahoe PK, Mullerian inhibiting substance in reproduction and cancer. Molecular Reproduction and Development, 1992, vol. 32, No. 2, pp. 168-172.*
Donahoe (Molecular Reproduction and Development, 1992, vol. 32, No. 2, pp. 168-172) Full Document.*
Coskun et al. (Journal of assisted reproduction and genetics, Jul. 1998, vol. 15, No. 6, pp. 372-377, Abstract Only).*
Pellicer et al. (Journal of in vitro fertilization and embryo transfer. IVF, Aug. 1987, vol. 4, No. 4, pp. 205-217).*
van Rooij, I.A. et al., *Serum Anti-Müllerian Hormone Levels: A Novel Measure of Ovarian Reserve*, Human Reproduction, vol. 17, No. 12, pp. 3065-3071 (2002).
Fanchi, Renato et al., "Serum Anti-Müerian Hormone Dynamics During Controlled Ovarian Hyperstimulation," *Human Reproduction*, vol. 18, No. 2, pp. 328-332, 2003.
de Vet, Annemarie et al., *Antimüllerian Hormone Serum Levels: A Putative Marker for Ovarian Aging*, Fertility and Sterility, vol. 77, No. 2, pp. 357-362 (2002).
McGee, Elizabeth A. et al., *Müerian Inhibitory Substance Induces Growth of Rat Preantral Ovarian Follicles*, Biology of Reproduction, vol. 64, pp. 293-298 (2001).
Seifer, David B. et al., *Early Follicular Serum Müllerian-Inhibiting Substance Levels are Associated with Ovarian Response During Assisted Reproductive Technology Cycles*, Fertility and Sterility, vol. 77, No. 3, pp. 468-471 (2002).
Cook, Christine L. et al., *Serum Müllerian-Inhibiting Substance Levels During Normal Menstrual Cycles*, Fertility and Sterility, vol. 73, No. 4, pp. 859-861 (2000).
Seifer, David B. et al., *Mitochondrial Deletions in Luteinized Granulosa Cells as a Function of Age in Women Undergoing In Vitro Fertilization*, Fertility and Sterility, vol. 78, No. 5, pp. 1046-1048 (2000).
Sharara, Fady I. et al., *The Detection of Diminished Ovarian Reserve in Infertile Women*, Am. Journal of Obstertrics and Gynecology, vol. 179, No. 3, pp. 804-812 (1998).
Vigier, Bernard et al., *Production of Anti-Müllerian Hormone: Another Homology Between Sertoli and Granulosa Cells*, Endocrinology, vol. 114, No. 4, pp. 1315-1320 (1984).
Takahashi, Masahiko et al., *The Ontogeny of Mullerian Inhibiting Substance in Granulosa Cells of the Bovine Ovarian Follicle*, Biology of Reproduction, vol. 35, pp. 447-453 (1986).

(Continued)

*Primary Examiner*—Long V. Le
*Assistant Examiner*—Lisa V. Cook
(74) *Attorney, Agent, or Firm*—Barbara V. Maurer

(57) ABSTRACT

Methods and kits are provided for assessing the ovarian reserve and predicting the ovarian response to fertility treatments in a female subject. The serum levels of MIS are shown to be positively correlated with the production and retrieval of mature oocytes and serve as prognostic indicators for the female response to fertility treatment. The MIS levels can be monitored prior to and during fertility treatment and are useful to adjust the timing and dosage of treatments in order to produce optimal outcome in individual patients, to avoid ovarian hyperstimulation, or to indicate cancellation of an unsuccessful treatment. MIS can also be administered to women to stimulate follicle development and to prevent depletion of ovarian reserve.

1 Claim, 2 Drawing Sheets

OTHER PUBLICATIONS

Bezard J., et al., *Immunocytochemical Study of Anti-Müllerian Hormone in Sheep Ovarian Follicles During Fetal and Post-Natal Development*, Journals of Reproduction & Fertility, vol. 80, pp. 509-516, (1987), Great Britain.

Meyts, Rajpert-De et al., *Expression of Anti-Müllerian Hormone During Normal and Pathological Gonadal Development: Association with Differentiation of Sertoli and Granulosa Cells*, Journal of Clinical Endocrinology & Metabolism, vol. 84, No. 10, pp. 3836-3844, (1999).

Hudson, Peter L. et al., *An Immunoassay to Detect Human Mullerian Inhibiting Substance in Males and Females During Normal Development*, Journal of Clinical Endocrinology & Metabolism, vol. 70, No. 1, pp. 16-22, (1990).

Jusso, Nathalie et al., *An Enzyme Linked Immunoassay for Anti-Müllerian Hormone: A New Tool for the Evaluation of Testicular Function in Infants and Children*, Journal of Clinical Endocrinology & Metabolism, vol. 70, No. 1, pp. 23-27 (1990).

di Clemente, Nathalie et al., *Cloning, Expression, and Alternative Splicing of the Receptor for Anti-Müllerian Hormone*, Molecular Endocrinology, vol. 8, No. 8, pp. 1006-1020 (1995).

Baarends, Willy M. et al., *Anti-Müllerian Hormone and Anti-Müllerian Hormone Type II Receptor Messenger Ribonucleic Acid Expression in Rat Ovaries During Postnatal Development, the Estrous Cycle, and Gonadotropin-Induced Follicle Growth*, Endocrinology, vol. 136, No. 11, pp. 4951-4962 (1995).

Teixeira, Jose et al., *Developement Expression of a Candidate Müllerian Inhibiting Substance Type II Receptor*, Endocrinology, vol. 137, No. 1, pp. 160-165 (1996).

Kim, J. H. et al., *The Inhibitory Effects of Müllerian-Inhibiting Substance on Epidermal Growth Factor Induced Proliferation and Progesterone Production of Human Granulosa-Luteal Cells*, Journal of Clinical Endocrinology & Metabolism, vol. 75, No. 3, pp. 911-917 (1992).

Seifer, David B. et al., *Gonadotropin-Releasing Hormone Agonist-Induced Differences in Granulosa Cell Cycle Kinetics Are Associated With Alternations in Follicular Fluid Müllerian-Inhbiting Substance and Androgen Content*, Journal of Clinical Endocrinology & Metabolism, vol. 76, No. 3, pp. 711-714 (1993).

Durlinger, Alexandra L. et al., *Control of Primordial Follicle Recruitment by Anti-Müllerian Hormone in the Mouse Ovary*, Endocrinology, vol. 140, No. 12, pp. 5789-5796 (1999).

Lee, Mary M. et al., *Mullerian Inhibiting Substance in Humans: Normal Levels from Infancy to Adulthood*, vol. 82, No. 2, pp. 571-576 (1996).

Takahashi, Masahiko et al., *Müllerian Inhibiting Substances as Oocyte Meiosis Inhibitor*, Molecular and Cellular Endocrinology, vol. 47, pp. 225-234 (1986).

Cate et al, Isolation of the bovine and human genes for mullerian inhibiting substance and expression of the human gene in animal cells, Cell; 1986; 45:685-689 ABSTRACT only.

Hirshfield A N, Relationship between the Supply of primordial Follicles and the Onset of Follicular Growth in Rats, Biol Reprod 1994; 50: 421-428.

Lee and Donahoe, Mullerian Inhibiting Substance: A Gonadal Hormone with Multiple Functions, Endocrine Reviews 1993; 14(5): 152-164.

\* cited by examiner

Figure 1

Comparison of Groups of Women with ≤6 versus ≥11 Retrieved Oocytes*

|  | ≤ 6 Oocytes (n=28) | ≥ 11 Oocytes (n=79) | p |
|---|---|---|---|
| Age (yrs) | 35.2 ± 0.7 | 34.2 ± 0.4 | NS |
| Day 3 FSH (IU/L) | 5.9 ± 0.4 | 4.9 ± 0.2 | 0.01 |
| Day 3 Estradiol (pg/ml) | 41 ± 3 | 32 ± 1 | 0.003 |
| MIS (ng/ml) | 1.0 ± 0.4 | 2.5 ± 0.3 | 0.006 |
| $E_2$ max. (pg/ml) | 1720 ± 160 | 2950 ± 140 | ≤ 0.0001 |
| # Oocytes | 4.5 ± 0.2 | 19.7 ± 0.9 | ≤ 0.0001 |
| % Mature Oocytes | 92 ± 2 | 90 ± 1.4 | NS |

* Mean ± SEM

MULLERIAN INHIBITING SUBSTANCE LEVELS AND OVARIAN RESPONSE

CROSS-REFERENCE TO RELATED APPLICATIONS

The present utility application claims priority to provisional patent application U.S. Ser. No. 60/313,545, filed Aug. 20, 2001, the disclosure of which is incorporated by reference in its entirety herein.

GOVERNMENT INTEREST

This invention was funded in part by National Institutes of Health Grant number AG15425. The government may have certain rights in this invention.

FIELD OF THE INVENTION

The present invention relates to the field of reproductive technology, developmental and molecular biology and the assessment of women's reproductive status. In particular, the invention provides novel methods for predicting and monitoring a woman's response to fertility treatments, as well as for preventing the depletion of her ovarian reserve.

BACKGROUND OF THE INVENTION

Various publications or patents are referred to throughout this application or at the end of this specification to describe the state of the art to which the invention pertains. Each of these publications or patents is incorporated by reference herein.

Infertility is a disease that results in the abnormal functioning of the human reproductive system. It is defined as the inability to conceive after one year of unprotected intercourse or the inability to carry a pregnancy to live birth. According to the Centers for Disease Control (CDC), 2.1 million married couples suffer from infertility or other conditions that impair their ability to have children, and an estimated 6.1 million women of child bearing age in the United States are infertile.

Female fertility begins to decline many years prior to the onset of menopause despite continued regular ovulatory cycles. Although there is no precise definition of advanced reproductive age in women, infertility is more prevalent after the age of 35. Because the average age of childbearing has increased over the past thirty years as more women have pursued higher education and careers, an unprecedented number of women will have reached their late reproductive years by the time they are ready to start families. As a consequence, many will require the assistance of fertility treatments in order to conceive a child. With patients willing to invest thousands of dollars in treatments to fulfill their dreams of starting a family, infertility has become a $2 billion industry annually in the US.

With the exception of oocyte donation, all fertility treatments currently available to women unable to conceive naturally depend on the woman's ovarian reserve. The term "ovarian reserve" refers to a woman's current supply of ovarian follicle number and oocyte quality, and is closely associated with reproductive potential. In general, the greater the number of remaining eggs, the better the chance for conception. Conversely, low ovarian reserve greatly diminishes a patient's chances for conception. As a woman ages, her supply of eggs gradually declines over time until the eggs are depleted at menopause. Even before birth, a woman's eggs begin to diminish in number. The great majority of oocytes are lost after the fifth month of intrauterine life, when a maximum of about seven million eggs have been reported. At birth, both ovaries contain around one million primordial follicles. Reproductive life starts with approximately 0.5 million primordial follicles at menarche. Thereafter, loss of follicles takes place at a fixed rate of around 1000 per month, accelerating beyond the age of 35. The number of eggs continues to decline as the woman ages, until no eggs remain at the time of menopause.

The most important aspect of diminished ovarian reserve, and the associated decline in reproductive potential, is that its onset is highly variable. Ovarian function is unique for each individual, both in the number of years of peak reproductive performance as well as in the onset and progression of its decline. Some women with normal menstrual cycles will have difficulty conceiving in their late twenties or early thirties. Because of the high individual variability of ovarian status, it is vitally important for clinicians to assess an infertility patient's ovarian reserve. In fact, the assessment of a woman's ovarian reserve is one of the most critical factors in the infertility evaluation of patients of any age. Women with diminished ovarian reserve experience decreased responses to ovulation induction, require higher doses of gonadotropin, have higher IVF (In Vitro Fertilization) cycle cancellation rates, and experience lower pregnancy rates through IVF.

Currently available methods for assessing ovarian reserve can be classified into passive and dynamic tests. The goal of both approaches is to provide information regarding oocyte quality and quantity in order to assess whether a woman is a candidate for a particular course of infertility treatment. The standard passive test for ovarian reserve consists of the measurement of serum basal FSH and estradiol on day 3 of the menstrual cycle. An early follicular phase FSH level of less than 10 mIU/ml and an estradiol level of less than 80 pg/ml is typically considered indicative of normal ovarian reserve, although cutoff values for FSH as high as 20 to 25 mIU/ml have been reported because of the use of different FSH assay reference standards. It is difficult to establish absolute values that define how high FSH levels can be due to variations in laboratory assessments and treatment methods. Moreover, women with baseline values in the normal range may have diminished reserves and by the time an elevation in the FSH level is evident it could well be too late for them to achieve a pregnancy or have fertility treatment. Some women with a normal FSH can be completely unaware that their ovarian reserve is steadily declining and are lulled into a false sense of security with regard to their prospects of starting a family. Other passive tests of ovarian reserve are under investigation but have not yet been recommended for routine clinical use because of limited data on their prognostic value. In contrast to the static measurements of ovarian reserve, the clomiphene citrate challenge test (CCCT) is a dynamic approach. Its purpose is to stimulate the ovary to initiate egg production in response to the fertility drug clomiphene. Although the clomiphene citrate challenge test is generally considered to be more accurate than the basal serum FSH test, none of the currently available tests have been shown to accurately reflect ovarian reserve.

It is thus evident that there is a need for more accurate and reliable methods of predicting and monitoring a woman's response to infertility treatment. In addition, a new method that would prevent the depletion of ovarian reserve would be highly desirable in the field of reproductive technology.

BRIEF DESCRIPTION OF THE DRAWINGS

FIG. 1 shows a comparison of groups of women with ≦6 versus ≧11 retrieved oocytes. The women in the two groups were of similar age and their day 3 FSH values did not differ significantly. However, the serum Mullerian Inhibiting Substance (MIS) values of the women in the ≧11 oocyte group were 2.5 times higher than those of the group of women from whom fewer than 6 oocytes were retrieved. Thus, serum MIS levels are positively correlated with the number of mature oocytes produced and are a useful marker of ovarian reserve.

DETAILED DESCRIPTION OF THE INVENTION

Figure 2:
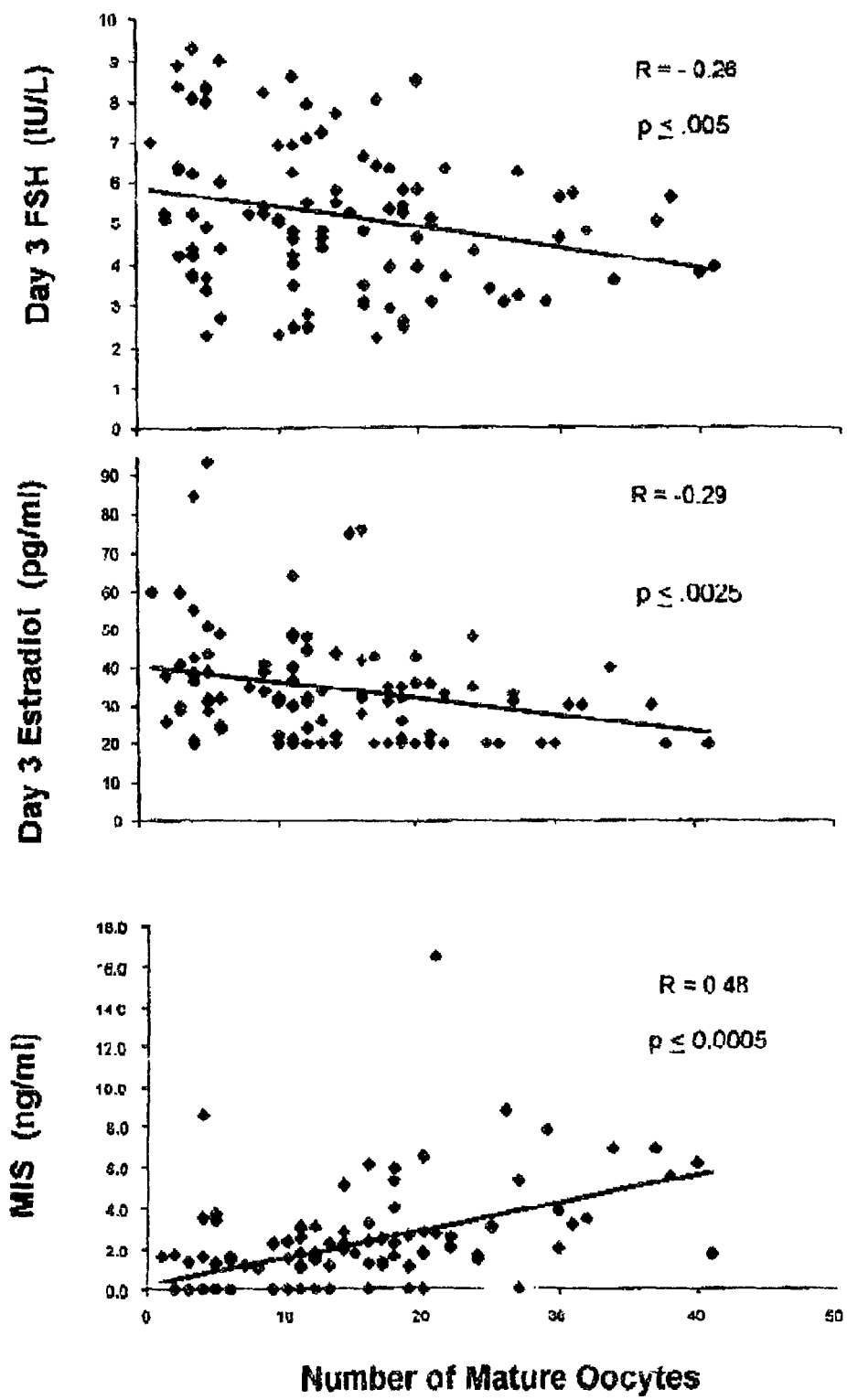
FIG. 2 shows the day 3 serum FSH, estradiol and MIS as a function of the number of mature oocytes recovered. The p values confirm the significance of these relationships and demonstrate that the highest correlation with number of oocytes is serum MIS concentration.

Currently, there is a great need for serum markers that accurately reflect the status of a woman's ovarian reserve. Contemporary serum markers for ovarian reserve include a combination of indirect (FSH) and a variety of direct hormones such as estradiol ($E_2$) or Inhibin B (Sharara et al., Am J. Obstet. Gynecol. 1998; 179: 804-812). Early follicular phase serum FSH reflects the activity of a blend of ovarian hormones ($E_2$, inhibins, activins, follistatins) that feedback to the hypothalamus and pituitary. Estradiol is secreted predominantly by granulosa cells within pre-antral and antral follicles. Inhibin B is secreted directly from granulosa within small antral follicles. Inhibin A is a product of luteinized granulosa cells of the dominant follicle and corpus luteum and influences early follicular serum FSH by its presence during the luteal-follicular transition. It is thus apparent that an additional drawback of the serum markers currently in clinical use is that they are predominantly a reflection of the developing FSH-dependent follicle as it progresses from its early antral to preovulatory states. Besides presenting difficulties with establishing clinically relevant values and reducing laboratory variations, the currently available serum markers that are based on the development of the FSH-dependent dominant follicle have limited value in assessing nongrowing ovarian follicle reserves.

A more accurate assessment of ovarian reserve necessarily involves determining the number of resting, FSH-independent primordial follicles. Resting primordial follicles continuously enter the growing follicle pool in the ovary throughout life. Animal studies have revealed that follicle loss is inversely related to the number of primordial follicles present in the ovaries (Hirshfield A. N., Biol. Reprod. 1994; 50: 421-428). Once follicles are stimulated to grow, they can either reach full maturation and ovulate or become atretic. The estimated time span of development between a primary and an early antral follicle in the human is thought to be several months, while the development from early antral stage to preovulatory follicles has been estimated to take approximately three months. In order to determine a woman's prospects of conceiving a child within the time frame of a typical fertility treatment (months to years), it is therefore more important to obtain a reliable estimate of the size of the pool of her primordial follicles, as opposed to assessing the small number of follicles that are rapidly approaching maturity and will be lost through the processes underlying ovulation in the current menstrual cycle.

Mullerian Inhibiting Substance (MIS) is a follicular fluid component produced by granulosa cells (Vigier et al., Endocrinology, 1984; 114: 1315-20; Takahashi et al., Biol. Reprod., 1986; 35: 447-53; Bezard et al., J. Reprod. Fertil., 1987; 80: 509-16; Rajpert-De Metys et al. J. Clin. Endocrinol. Metab 1999; 84: 3836-44) and is noted in human serum from early adolescence through adulthood but disappears at the menopause (Hudson et al., J Clin Endocrinol Metab 1990; 70: 16-22; Josso et al., J Clin Endocrinol Metab 1990; 70: 23-7; Lee et al. J. Clin. Endocrinol. Metab. 1996; 81: 571-6). Both the DNA and protein sequences of MIS are well known in the art (Lee and Donahoe, Endocrine Reviews 1993; 14(5): 152-164; Cate et al., Cell, 1986; 45: 685-689). MIS levels vary slightly with the menstrual cycle (Cook et al., Fertil Steril 2000; 73: 859-61), reaching a maximum in the late follicular phase.

MIS follicular fluid levels from women undergoing retrieval for in vitro fertilization have been measured demonstrating its presence in the preovulatory follicles of superovulated women (Seifer et al., J. Clin. Endocrinol. Metab. 1993; 76: 711-4). The MIS type II receptor is expressed in rodent granulosa cells (di Clemente et al., Mol Endocrinol 1994; 8: 1006-20; Baarends et al., Endocrinology 1995; 136: 4951-62; Teixeira et al., Endocrinology 1996; 137: 160-5), and MIS appears to act in a paracrine fashion to regulate granulosa cells and oocyte function (Takahashi et al., Mol Cell Endocrinol 1986; 47: 225-34; Kim et al., J. Clin. Endocrinol. Metab. 1992; 75: 911-7; Seifer et al., J. Clin. Endocrinol. Metab. 1993; 76: 711-4). A recent study using MIS knockout mice demonstrated that MIS null females and those heterozygous for the MIS null mutation had a relatively early depletion of their pool of primordial follicles (Durlinger et al., Endocrinology 1999; 140: 5789-96). Such work supports the role of MIS as a regulator of primordial follicle recruitment, implying that MIS secretion reflects the size of the primordial pool. A serum marker that is indicative of the primordial pool of nongrowing FSH-independent follicles before initiation would be very useful in the prediction of eventual ovarian response to ovulation induction medications used in preparation for an assisted reproductive techniques cycle.

Accordingly, the present invention provides a novel method of correlating serum MIS levels with ovarian reserve, as well as novel methods of predicting ovarian response in women undergoing ovulation induction as part of an ART cycle. The methods of the, invention allow the clinician to accurately predict which women will be good and which will be poor responders to currently available infertility treatments. Furthermore, the invention provides methods of monitoring the ovarian response of women during fertility treatments. This will allow for the more accurate planning and timing of oocyte retrieval, resulting in fewer canceled cycles and significantly reducing the financial and emotional costs of fertility treatments. Because the average in vitro fertilization cycle charges are between $10,000 and $17,000, the methods of the invention will lead to a substantial reduction in costs for patients and insurers. Importantly, the invention also provides for methods of predicting, monitoring, and preventing ovarian hyperstimulation syndrome. Ovarian hyperstimulation syndrome (OHSS) is characterized by a group of disorders that can range from mild to severe and potentially life-threatening symptoms. OHSS often includes severe pelvic pain, abdominal distention, ovarian enlargement, hemoconcentration ascites, pleural or pericardial effusions, or both, renal failure, oligourea, hypercalemia, and hypercoagulation. It most often is associated with the administration of exogenous gonadotropins. The kits and methods of the present invention allow the clinician to prevent ovarian hyperstimulation syndrome, as by the elimination of hCG administration. Thus, by measuring MIS levels, the clinician can make an informed decision to administer hCG because of the risk of ovarian hyperstimulation. Another course of action in the prevention of ovarian hyperstimulation syndrome is to freeze the embryos rather than to transfer them back into the patient, a process known as cryopreservation. By the methods of the invention, pregnancy can be delayed and hCG levels kept to a minimum until the risk of ovarian hyperstimulation by excess hCG has passed.

Finally, the invention provides methods of preventing the depletion of ovarian follicle reserves and methods for stimulating follicle development, thereby treating infertility in women.

The methods of the present invention can be applied to obtain results that predict good, sub-optimal or poor responses to fertility treatments. The methods are thus highly useful for clinical application as a guide for determining the optimal dose of fertility drugs for women undergoing in vitro fertilization (IVF) treatment. IVF clinics usually rely on patient age as the only index for specifying the quantity of fertility drugs to be administered. Age, however, is a nonspecific and unreliable indicator of the ovarian response and the present invention represents a significant improvement over the currently available diagnostic tools. The methods of the present invention can be applied to all patients prior to undergoing IVF treatment in order to identify poor responders and therefore reduce cancellation rate as well as to identify excessive responders and therefore reduce the risk of hyperstimulation. The invention thus allows adjustments to be made to the ovarian stimulation regime to compensate for a diminished ovarian reserve in women identified as sub-optimal responders.

In one aspect the invention provides a method of correlating serum MIS levels with ovarian reserve. The correlation between MIS levels and ovarian reserve may be obtained by determining the number of oocytes retrieved from a particular subject and determining that subject's serum levels of MIS and choosing a graphical representation for the data obtained. Tools for effective and efficient analysis and representation of data are well known in the art. They include the use of statistics to analyze the data and estimate errors, and the use of computers to implement these techniques and other methods of analysis. Further, the graphical representation of the data and functions may include the use of tables, charts and other diagrams, as well as computer programs to make calculations and produce the charts, graphs, and tables.

Another aspect of the present invention includes a method of assessing ovarian reserve in a female seeking fertility treatment by determining the serum MIS level in the female and comparing the determined level to the data correlating MIS serum level with number of mature oocytes retrieved. An exemplary representation of data correlating MIS serum levels with the number of mature oocytes retrieved is the chart depicted in FIG. 2. By determining the serum MIS level and its correlated oocyte retrieval value, the ovarian reserve of the female can be reliably assessed and an appropriate fertility treatment protocol can be selected.

In a related aspect the invention provides a diagnostic kit for determining a woman's ovarian reserve by measuring her serum MIS level and correlating the MIS level obtained with the empirical value of mature oocytes retrieved by the use of statistical data such as that represented by the graph provided in FIG. 2. Measurement of the serum MIS level can be accomplished by the use of monoclonal or polyclonal antibodies specific for MIS and may include labeling reagents for the MIS-specific antibodies. In addition, the MIS receptor and peptides derived therefrom may be used to detect MIS levels. The kit may further include instructions for its use.

Another preferred embodiment is a method of predicting a woman's ovarian response to ovulation induction by determining her serum MIS level and comparing the determined level to a standard level; thereby predicting ovarian response to ovulation induction. In a related embodiment the present invention provides a kit for predicting ovarian response to ovulation induction. The kit includes reagents such as monoclonal and polyclonal antibodies specific for MIS and labeling substances for determining a serum MIS level, as well as a chart for correlating any particular serum MIS level with the number of mature oocytes likely to be retrieved. The kit may further comprise instructions for its use and for the interpretation of the data obtained.

In the present invention, a method and kit for measuring serum MIS levels in a female subject as a prognostic indicator of ovarian response to hyperstimulation are contemplated. The method and kit may use a monoclonal and/or polyclonal antibodies to MIS as diagnostic reagents for measuring physiological MIS levels as a prognostic indicator of oocyte quantity and, importantly, of oocyte quality. The higher the concentration of endogenous MIS produced by the female subject, the greater her inherent reproductive potential, given that increased levels of MIS positively correlate to reproductive potential. See FIGS. 1 and 2.

A further embodiment of the present invention is a method of stimulating follicle development in a woman by administering MIS to the female subject. For purposes of clinical administration, the MIS may be combined with a pharmaceutically acceptable carrier. The method of MIS administration may be by parenteral route or any other medically suitable route. In the average human female, only about 400 follicles reach the mature preovulatory stage and ovulate in a lifetime. The vast majority of follicles over a woman's lifetime are lost through a process known as atresia with programmed cell death as the underlying molecular mechanism rather than through growth and subsequent ovulation. Thus, stimulating the growth of follicles through the administration of MIS may rescue a certain percentage of follicles that would otherwise be destined to undergo apoptosis. The enhanced survival of these follicles will increase a woman's ovarian reserve and improve her chances of success in the fertilization treatment.

In a related embodiment, the invention provides a method of modifying gonadotropins in a female subject, comprising administering MIS to the subject. The importance of gonadotropins and various growth factors to suppress apoptosis has been the subject of intensive investigation. FSH has been shown to decrease apoptosis in granulosa cells obtained from hypophysectomized rats and to prevent apoptotic changes of cultured preovulatory follicles (Chun S. Y. et al., Endocrinology 1994; 135:1845-1853).

Another preferred embodiment of the invention is a method of identifying a good responder to infertility treatment, comprising determining the serum MIS level in a subject. An important advantage provided by the invention is the ability to differentiate between women exhibiting elevated FSH levels who, under current practice, would be discouraged from attempting fertility treatments. Thus, the invention enables clinicians to identify potential responders among subjects whose conventional diagnostic values are suboptimal.

In yet another embodiment, the invention provides a kit for identifying the quantity, presence, or absence of MIS to monitor the use of ovulation induction medications and to predict outcome.

One aspect of the present invention is a method of treating infertility in vivo using MIS to stimulate follicle development and therefore oocyte production and maturation, which ultimately leads to increased fertility in female subjects. The MIS type II receptor is expressed in rodent granulosa cells and MIS acts in a paracrine fashion to regulate granulosa cells and oocyte function. Because of the location of the receptor for MIS, a therapeutically effective dose of MIS is preferably administered either directly to the ovarian follicles or parenterally to another part of the subject so that the MIS reaches the ovary.

A therapeutically effective dose of a MIS for administration in vivo is typically formulated with a pharmaceutically acceptable carrier, meaning one that is non-toxic to recipients at the dosages and concentrations employed and is compatible with other ingredients of the formulation. For example, the formulation would not contain any substances that are known to be deleterious to MIS. The carrier may contain additives such as substances that enhance isotonicity and chemical stability. The additive materials may include buffers such as phosphate, citrate, succinate, acetic acid, and other organic acids or their salts; antioxidants such as ascorbic acid; low molecular weight (less than about twelve residues) polypeptides, proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, trehalose, glucose, mannose, or dextrins; chelating agents such as EDTA; sugar alcohols such as mannitol or sorbitol; counter-ions such as sodium; and/or nonionic surfactants such as polysorbates, poloxamers, or PEG. The final MIS preparation may be a liquid or lyophilized solid. The MIS, a suitable derivative or a metabolite thereof may be used alone or in admixture with one or more additional active agents.

The MIS and therapeutic compositions thereof discussed in the methods of the present invention are also suitably administered by sustained-release systems, such as semipermeable polymer matrices in the form of shaped articles, like microcapsules. Sustained-release matrices include polylactides, copolymers of L-glutamic acid and gamma-ethyl-L-glutamate, poly (2-hydroxyethyl methacrylate), ethylene vinyl acetate or poly-D-(−)-3-hydroxybutyric acid. Sustained-release compositions also include liposomally entrapped compounds. The liposomes are preferably about 200-800 Angstroms unilamellar type.

MIS to be used for therapeutic administration is preferably sterile, and this may be achieved using filtration through sterile filtration membranes of about a 0.2 micron size. Therapeutic MIS compositions generally are placed into a container having a sterile access port, for example, an intravenous solution bag or vial having a stopper pierceable by a hypodermic injection needle. The above formulations are also suitable for in vitro uses.

MIS ordinarily will be stored in unit or multi-dose containers, for example, sealed ampules or vials, as an aqueous solution, or as a lyophilized formulation for reconstitution. As an example of a lyophilized formulation, 10-mL vials are filled with 5 mL of sterile-filtered 1% (w/v) aqueous MIS solution, and the resulting mixture is lyophilized.

The therapeutically effective dose of MIS in the present invention will generally be in the range of about 0.01 µg/kg to about 100 mg/kg per day. Preferably, from 0.1 to 1 µg/kg. A clinician will administer the MIS formulations of the invention until a dosage is reached that improves the infertility condition, taking into account the usual factors of age, body weight, health, and other factors individual to the subject. The progress of this therapy is easily monitored by conventional assays.

An additional aspect of the invention is to improve the quality and fertility of oocytes. In this aspect of the invention, the oocytes may be improved either in vivo or ex vivo. In this aspect, the oocytes may be either immature or fully developed. This invention may be used on human or non-human female animal subjects. If used on human subjects, the preferred method is used with subjects who are infertile, who can not conceive without clinical intervention, or subjects who may not be able to conceive without clinical intervention in the future, such as subjects preparing to undergo chemotherapy. If used on non-human subjects, the method is preferably used on animals in captivity and most preferably on endangered species.

The ex vivo methods of the present embodiment first require removing the oocytes, preferably immature oocytes, from follicles in the ovary. This may be accomplished by conventional techniques, such as using the natural cycle or ovulation induction methods, during surgical intervention such as oophorerectomy, during hyperstimulation protocols in the context of an IVF program, or by necropsy. In the natural cycle, ultrasound or laparoscopy allows identification of one or more burgeoning follicles on the ovarian surface near midcycle. The follicles approaching ovulation are distended and substantially translucent. The follicles are then aspirated with a needle and one or more oocytes are extracted transvaginally. The oocytes are then evaluated based on the number and density of surrounding granulosa cells, the presence or absence of the first polar body, and the thickness of the zona pellucida, as well as other factors.

The invention also contemplates improving the fertility of already maturing oocytes including oocytes from hormone stimulated subjects, so that the oocytes are more mature than oocytes from unstimulated ovaries. Agents used to induce such controlled multiple follicular maturation include inhibin administered directly to the ovary, clomiphene citrate or human menopausal gonadotropins, or a mixture of FSH and LH, and/or human chorionic gonadotropins. These fertility agents are administered in therapeutically effective amounts. A gonadotropin releasing hormone agonist or antagonist may also be used in conjunction with FSH.

In this aspect after extraction, therapeutically effective doses of MIS are administered to the oocyte. The MIS preferably binds to its receptors on the granulosa cells and/or oocytes and stimulate the growth and maturation of the oocytes, leading to mature, healthy oocytes ready for fertilization. The MIS to be administered will be either alone or preferably mixed with a pharmaceutical carrier. If the inventive method occurs in vivo, the subject will preferably produce one or more mature, healthy oocytes that are primed for fertilization. If the inventive method occurs in vitro, the oocyte will mature and will be fertilized with sperm at the appropriate time. When the resulting embryo reaches a 4-8 cell stage or as a blastocyst, it is preferably implanted in the carrier and develops until birth.

DEFINITIONS

Various terms relating to the present invention are used throughout the specification and claims.

As used herein, "MIS" refers to Mullerian inhibiting substance from any species, including murine, bovine, ovine, porcine, equine, avian, and preferably human, in native sequence or in a genetically engineered form, and from any source, whether natural, synthetic, or recombinantly produced.

The term "parenteral" refers to introduction of the polypeptide by intravenous, intraarterial, intraperitoneal, intramuscular, intraventricular, intracranial, subcutaneous, subdermal, transvaginal, oral, nasal, or rectal routes.

"Therapeutically effective dose" is a dose that produces the effects for which it is administered.

"Paracrine" is a form of signaling in which the target cell is close to the signal-releasing cell.

As used herein, the term "oocyte" refers to the gamete from the follicle of a female animal.

"Antibodies" as used herein includes polyclonal and monoclonal antibodies, chimeric, single chain, and humanized antibodies, as well as Fab fragments, including the products of a Fab or other immunoglobulin expression library.

"Monoclonal antibodies" are substantially homogenous populations of antibodies to a particular antigen. They may be obtained by any technique that provides for the production of antibody molecules by continuous cell lines in culture. Monoclonal antibodies may be obtained by methods known to those skilled in the art. See, for example, Kohler, et al., Nature 256:495-497, 1975, and U.S. Pat. No. 4,376,110.

"Polyclonal antibodies" are a group of heterogeneous antibodies produced by different B lymphocytes in response to the same antigen, wherein different antibodies in the group recognize different parts of the antigen.

"Gonadotropins" are a group of glycoprotein hormones from the anterior lobe of the pituitary gland. They stimulate growth of the gonads and the secretion of sex hormones. Examples of gonadotropins include, among others, substances such as follicle stimulating hormone (FSH), luteinizing hormone (LH), chorionic gonadotrophin (hCG).

The terms "standard" and "standard level" are used herein to define a determined concentration of MIS obtained from taking a number of readings, preferably a statistically significant number of readings such as depicted in FIG. 2. The standard can be arbitrarily fixed depending on the degree of success a reading above or below the standard is to indicate.

EXAMPLES

The following examples are provided to better illustrate the claimed invention and are not to be interpreted as limiting the scope of the invention. To the extent that specific materials are mentioned, it is merely for purposes of illustration and is not intended to limit the invention.

Example 1

Day 3 serum samples that had been stored at −80° C. between March 1999 and March 2001 were thawed and assayed in batches for MIS. One sample was analyzed from each of 107 women who had serum drawn within 2 months of undergoing pituitary desensitization with leuprolide acetate (Lupron; TAP Pharmaceuticals, North Chicago, Ill.) followed by gonadotropin stimulation in preparation for IVF. Details of stimulation protocol were similar to those described in a previous publication (Seifer et al., J. Clin. Endocrinol. Metab. 1993; 76:711-4). Follicle-stimulating hormone stimulation was used almost exclusively for gonadotropin stimulation. Occasionally, leuprolide acetate was stopped once gonadotropins were initiated. The two groups studied consisted of 28 samples from women who had $\leq 6$ oocytes (range, 1-6 oocytes) and 79 samples from women who had $\geq 11$ oocytes (range, 11-44 oocytes) retrieved.

Selection criteria of $\leq 6$ and $\geq 11$ retrieved oocytes were arbitrarily chosen in an effort to exaggerate potential physiologic differences among groups of women with different ovarian response. Serum from women with elevated FSH ($\geq 10$ IU/L) were excluded in an effort to determine whether day 3 serum MIS may be associated with number of oocytes retrieved within a "normal" range of day 3 serum FSH values. Follicles measuring $\geq 18$ mm in diameter were aspirated under patient sedation 36 hours after hCG injection. This study was exempt from institutional review board approval because serum samples had been stored as part of laboratory quality assurance and as such were considered to be clinically discarded material.

Example 2

Mullerian-Inhibiting Substance ELISA

The ELISA used to measure human MIS has been extensively described (Hudson et al., J. Clin. Endocrinol. Metab. 1990; 70: 16-22; Lee et al. J. Clin. Endocrinol. Metab. 1996; 81: 571-6). Samples were analyzed in duplicate at six serial dilutions; the results reported are the mean of three dilutions falling within the linear portion of the standard curve, constructed using four-parameter logistical curve fitting DeltaSoft II (BioMetallics, Inc., Princeton, N.J.). The sensitivity of this assay was 0.5 ng/mL; the intra-assay and interassay coefficients of variation are 9% and 15%, respectively. The MIS ELISA does not recognize LH, FSH, activin, inhibin, or TGF-$\beta$ and does not cross-react with bovine or rodent MIS (Hudson et al., J. Clin. Endocrinol. Metab. 1990; 70: 16-22).

Example 3

Statistical Analysis

Serum values are expressed as mean±standard error of the mean (SEM) in all cases. An unpaired t test performed by StatView (Abacus Concepts, Inc., Berkeley, Calif.) was used to determine whether differences between compared groups were statistically significant. Differences with P values of $\leq 0.05$ were considered statistically significant. The correlations between serum MIS and FSH, $E_2$, numbers of oocytes retrieved, and numbers of mature oocytes retrieved were determined by constructing linear curve fits of the data plotted on linear axes. The slopes of the resulting lines were tested for statistically significant difference from zero by obtaining their P values from the tables of critical values for the corresponding correlation coefficients.

RESULTS

A comparison of mean ages, day 3 serum FSH, $E_2$, MIS, stimulation cycle $E_2$ max concentrations, and the number of oocytes between women with $\leq 6$ oocytes and those with $\geq 11$ retrieved oocytes is summarized in FIG. 1. Mean age was similar among groups. Although mean±SEM day 3 serum FSH (5.9 IU/L±0.4 vs. 4.9 IU/L±0.2) and mean day 3 serum $E_2$ (41 pg/mL±3 vs. 32 pg/mL±1) were statistically significantly different (P=0.01 and P=0.003, respectively), the differences in their respective values were not clinically significant. The maximum $E_2$ levels reached were significantly greater in the high-oocyte number group (2,950 pg/mL±140 vs. 1,720 pg/mL±160; P≦0.0001). Mean MIS concentrations were 1.0 ng/mL±0.4 vs. 2.5 ng/mL ±0.3, or a >2.5-fold greater concentration of MIS (P=0.006) between groups (Table 1).

Correlation between serum MIS and other measures of ovarian function demonstrated statistically significant inverse relationships between MIS and day 3 $E_2$ (r=−0.169, P≦0.05) and FSH (r=−0.295, P≦0.005). Statistically significant positive correlations between MIS and numbers of oocytes retrieved (r=0.522, P≦0.001) and the maximum serum E2 concentration (r=0.328, P≦0.001) obtained during ovulation induction were noted.

Furthermore, day 3 serum MIS, but not $E_2$ or FSH, was positively correlated with the number of mature oocytes ultimately retrieved (FIG. 1). Although all correlations were statistically significant, the MIS correlation (r=0.48, P≦0.0005) was considerably stronger than that of either of the other markers of ovarian reserve (i.e., $E_2$ or FSH).

DISCUSSION

Mullerian-inhibiting substance is a dimeric glycoprotein and member of the transforming growth factor β superfamily of growth factors. It is produced by ovarian granulosa cells (Vigier et al., Endocrinology 1984; 114: 1315-20; Takahashi et al., Biol. Reprod. 1986; 35: 447-53; Bezard et al. J. Reprod. Fertil. 1987; 80: 509-16; Rajpert-De Meyts et al., J. Clin. Endocrinol. Metab. 1999; 84: 3836-44) and is noted in human serum from early adolescence through adulthood but disappears at the menopause (Hudson et al., J. Clin. Endocrinol. Metab. 1990; 70: 16-22; Josso et al., J. Clin. Endocrinol. Metab. 1990; 70: 23-7; McGee et al., Biol. Reprod. 2001; 64: 293-8). Mullerian-inhibiting substance follicular fluid levels from women undergoing retrieval for IVF have been measured, demonstrating its presence in the preovulatory follicles of superovulated women (Seifer et al., J Clin Endocrinol Metab 1993; 76: 711-4).

The data demonstrate for the first time an association between early follicular phase serum MIS and the number of retrieved oocytes, despite clinically similar day 3 serum FSH and $E_2$ concentrations. Specifically, higher serum MIS concentrations were associated with greater number of retrieved oocytes. Furthermore, day 3 serum MIS was associated with number of retrieved oocytes and number of mature oocytes despite so-called normal-range day 3 serum FSH of ≦10 IU/L. Serum MIS concentration may reflect the size of the primordial follicle pool and hence, may provide a marker associated with the anticipated number of oocytes to be retrieved after controlled ovarian stimulation for IVF. It remains unclear what the relative contributions of the primordial pool and the preantral and early antral follicles may have in determining the serum concentration of MIS on day 3 of the cycle. Because MIS expression begins in the third trimester of gestation (Rajpert-De Metys et al. J. Clin. Endocrinol. Metab 1999; 84: 3836-44), actually long before it can be detected in serum, it is likely that MIS plays a significant role in early follicular development at a time much sooner than previously thought. Furthermore, MIS expression most likely continues in most, if not all, follicles after birth and well before gonadotropin effects.

Once ovarian cycles begin, however, serum MIS levels vary slightly from a stable baseline value (Cook et al., Fertil. Steril. 2000; 73: 859-61), presumably as a result of the stimulation of a small cohort of follicles and the loss of MIS production as the corpus luteum is formed. Early follicular phase MIS levels result from the pool of follicles that began producing MIS in utero independently of the hypothalamic-pituitary axis and therefore may be considered distinct from other gonadotropin-dependent indicators of ovarian reserve.

The invention demonstrates that day 3 serum MIS may offer a clinical contribution to the set of serum markers currently used for assessing ovarian reserve. Such a marker of the primordial pool status may provide a unique perspective not available by current serum markers nor directly measurable by ultrasound. This possibility is supported by two recent reports that conclude that MIS induces follicular growth (Durlinger et al., Endocrinology 1999; 140: 5789-96; McGee et al., Biol. Reprod. 2001; 64: 293-8). The invention contemplates additional studies that examine cancellation rates and pregnancy outcomes in larger patient populations.

What is claimed is:

1. A method of predicting ovarian reserve prior to ovulation induction in a subject in need of ovulation induction, comprising:
    (a) determining a serum Mullerian inhibiting substance (MIS) level in a subject prior to ovulation induction;
    (b) comparing the determined serum MIS level to a standard which correlates MIS serum level to the number of oocytes obtained after ovulation induction; and
    (c) predicting ovarian reserve prior to ovulation induction in the subject in need of ovulation induction, wherein increased serum MIS is indicative of increased number of mature oocytes.

* * * * *